United States Patent
Kitano

(10) Patent No.: US 9,113,045 B2
(45) Date of Patent: Aug. 18, 2015

(54) ELECTRONIC ENDOSCOPIC APPARATUS AND CONTROL METHOD THEREOF

(71) Applicant: FUJIFILM Corporation, Tokyo (JP)

(72) Inventor: Ryou Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 382 days.

(21) Appl. No.: 13/754,482

(22) Filed: Jan. 30, 2013

(65) Prior Publication Data

US 2013/0222563 A1    Aug. 29, 2013

(30) Foreign Application Priority Data

Feb. 27, 2012    (JP) .................................. 2012-040437

(51) Int. Cl.
| | |
|---|---|
| H04N 9/47 | (2006.01) |
| H04N 7/18 | (2006.01) |
| A62B 1/04 | (2006.01) |
| A61B 1/045 | (2006.01) |
| G02B 23/24 | (2006.01) |

(Continued)

(52) U.S. Cl.
CPC .............. *H04N 7/18* (2013.01); *A61B 1/00188* (2013.01); *A61B 1/045* (2013.01); *G02B 7/10* (2013.01); *G02B 23/2438* (2013.01); *G02B 23/2469* (2013.01); *G02B 23/2484* (2013.01); *A61B 1/00009* (2013.01)

(58) Field of Classification Search
USPC ........... 348/65, 64, 63, 61, 72, 77, 79, 50, 49, 348/45, 143, 156, 184, 208.6, 211.8, 211.9, 348/211.13, 229.1, 231.6, 240.1, 240.3, 348/240.99, 333.01, 425.1, 561, 658; 600/101, 104, 117, 118, 132, 134, 164, 600/301, 920; 606/46, 35, 11
See application file for complete search history.

(56) References Cited

U.S. PATENT DOCUMENTS

| | | | |
|---|---|---|---|
| 5,290,283 A * | 3/1994 | Suda ............................. | 606/37 |
| 2003/0016301 A1 | 1/2003 | Aizaki et al. | |

(Continued)

FOREIGN PATENT DOCUMENTS

| | | |
|---|---|---|
| DE | 102010027905 A1 | 10/2011 |
| JP | 11-313247 A | 11/1999 |

(Continued)

OTHER PUBLICATIONS

Japanese Office Action (including partial English language translation thereof), dated Dec. 24, 2013, for corresponding Japanese Patent Application No. 2012-040437.

*Primary Examiner* — Jefferey Harold
*Assistant Examiner* — Mustafizur Rahman
(74) *Attorney, Agent, or Firm* — Birch, Stewart, Kolasch & Birch, LLP

(57) ABSTRACT

An electronic endoscopic apparatus includes an endoscopic scope, an imaging device provided in the endoscopic scope, a signal processing unit processing a captured image signal obtained by the imaging device to generate an observation image, a monitor device displaying the observation image, and a control unit controlling the signal processing unit to generate a high definition observation image and a high sensitivity observation image as the observation image, in which the control unit makes the signal processing unit generate the high sensitivity observation image at the time of screening the inside of the biological body, and generate the high definition observation image at the time of precise inspecting for an interest area in the body.

7 Claims, 9 Drawing Sheets

(51) Int. Cl.
*G02B 7/10* (2006.01)
*A61B 1/00* (2006.01)

(56) References Cited

U.S. PATENT DOCUMENTS

| | | | |
|---|---|---|---|
| 2007/0134866 A1* | 6/2007 | Huang et al. | 438/199 |
| 2008/0071142 A1* | 3/2008 | Gattani et al. | 600/117 |
| 2008/0151367 A1* | 6/2008 | Aizaki et al. | 359/389 |
| 2011/0184236 A1 | 7/2011 | Yoshino | |
| 2011/0228069 A1* | 9/2011 | Mimura et al. | 348/79 |

FOREIGN PATENT DOCUMENTS

| | | |
|---|---|---|
| JP | 2001-292369 A | 10/2001 |
| JP | 2004-267580 A | 9/2004 |
| JP | 2007-251694 A | 9/2007 |
| JP | 2008-72501 A | 3/2008 |
| JP | 2011-147707 A | 8/2011 |

* cited by examiner

| g1 | g2 | g5 | g6 |
| g3 | g4 | g7 | g8 |
| g9 | g10 | g13 | g14 |
| g11 | g12 | g15 | g16 |

FIG. 11

| R | G | Ⓡ | G | R |
| G | △B | ▢G | △B | G |
| Ⓡ | ▢G | R | ▢G | Ⓡ |
| G | △B | ▢G | △B | G |
| R | G | Ⓡ | G | R |

ELECTRONIC ENDOSCOPIC APPARATUS AND CONTROL METHOD THEREOF

CROSS-REFERENCE TO RELATED APPLICATIONS

This application claims the benefit of Japanese Patent Application No. 2012-040437 filed on Feb. 27, 2012, the entire contents of which are hereby incorporated by reference.

BACKGROUND OF THE INVENTION

1. Technical Field

The present invention relates to an electronic endoscopic apparatus and a control method thereof.

2. Related Art

For CCD type or CMOS type image sensors (imaging devices) to be mounted in a digital camera, the number of pixels has been increased such that a subject image can be imaged with high definition. An image sensor mounted in a front-end part of a scope of an electronic endoscopic apparatus is no exception to the trend of the increasing the number of pixels, and the number of pixels has been increased for the purpose of improving the descriptiveness of a minute structure such as, for example, blood vessels.

Specifically, in an area that a doctor is interested in, for example, a subject or an interior wall of a biological body located at the center of a screen and brightened by an illuminating light (hereinafter, referred to as an "interest area"), the increase of the number of pixels benefits as the high definition of a captured image. However, because the pixel size of each pixel is decreased due to the increase of the number of pixels, there is a problem in that the amount of light capable of being received in a light receiving surface per one pixel is decreased, and thus, the sensitivity of a captured image is sacrificed.

Meanwhile, in a non-interest area, for example, the inside in a biological body or a periphery of a screen, in which the amount of the illuminating light is not sufficient, it is more important to realize a change in color such as, for example, a rube, or a change in structure such as, for example, a polyp than to inspect a high definition image in detail. That is, a captured image become required that places priority to a screening to find a new interest area. Therefore, the sensitivity of a captured image becomes more important than the precision of the captured image.

In case of a digital camera, as disclosed in, for example, JP-A-2008-072501 and JP-2007-251694, a high definition image is generated based on detection signals of each individual pixel in the bright area within one imaging screen, and pixel addition is performed to add detection signals of a plurality of pixels while sacrificing the precision in order to place priority to the sensitivity in the dark area within the screen.

JP-A-H11-313247 discloses that the pixel addition performed in the digital camera is also performed in an electronic endoscope. However, in the electronic endoscope, even if whether to perform the pixel addition only based on the brightness or the number of pixel addition is determined, it is not the pixel addition that meets an intended use of the electronic endoscope. That is because the photographing environment for using the electronic endoscope is substantially different from that for the digital camera.

The front-end part of the scope of an image sensor built-in electronic endoscope is inserted and used within a biological body. That is, the front-end part of the scope is used in a dark environment. For this reason, the imaging is performed while illuminating light is illuminated to an area to be observed from a light source built in the front-end part of the scope or a light guide inserted through the endoscopic scope.

The brightness of the area illuminated by the illuminating light is greatly changed depending on whether a direction where the front-end part of the scope is headed, i.e., the illuminating direction of the illuminating light faces a wall within the biological body or an inner side within the biological body. The ratio of the brightness may be, for example, a ratio of 2000:1. With the endoscope, an observation at the time of precise inspecting that carefully observes a region for a long time and an observation at the time of screening time that observes the images obtained while inserting the endoscopic scope into the biological body, are often alternately performed.

In the observation at the time of screening when the brightness is occasionally changed from time to time in the above described ratio of 2000:1, it is difficult to obtain a good observation image. Therefore, the light emitting amount is controlled in the electronic endoscope in order to reduce the change of the brightness according to the insertion of the endoscopic scope. Further, in the observation at the time of precise inspecting, an enlarged image is observed by locating the front-end part of the scope close to the interest area such as, for example, a lesion part to illuminate the illuminating light.

Because such a photographing environment distinct to the endoscope exist, it is required to perform the pixel addition control by adding a factor in addition to the brightness suitable for an intended use of the endoscope, rather than to determine the pixel addition number and a pixel addition area merely based on the brightness.

SUMMARY OF THE INVENTION

An object of the present invention is to provide an electronic endoscopic apparatus and a control method thereof in which whether to image a high sensitivity image or a high definition image is determined based on a factor other than the brightness and a factor suitable for the observation image of the endoscope.

According to an aspect of the invention, an electronic endoscopic apparatus includes an endoscopic scope that is insertable into a biological body, an imaging device that is provided in the front-end part of the endoscopic scope, a signal processing unit that processes a captured image signal obtained by the imaging device to generate an observation image, a monitor device that displays the observation image, and a control unit that controls the signal processing unit to generate a high definition observation image and a high sensitivity observation image as the observation image. The high sensitivity observation image is constituted by pixel data corresponding to those obtained by combining n data selected from pixel data constituting the high definition observation image as one set. The control unit makes the signal processing unit generate the high sensitivity observation image at the time of screening the inside of the biological body by the endoscopic scope, and generate the high definition observation image at the time of precise inspecting for an interest area in the biological body. N is a natural number equal to or more than 2.

According to another aspect of the invention, a control method of an electronic endoscopic apparatus in which an observation image is generated by a signal processing unit that processes a captured image signal from an imaging device accommodated in the front-end part of an endoscopic scope insertable into a biological body, and is displayed on a monitor device, includes controlling the signal processing unit to generate a high definition observation image and a high sensitivity observation image as the observation image. The high sensitivity observation image is constituted by pixel data corresponding to those obtained by combining n data among pixel data constituting the high definition observation image as one set. At the controlling step, at the time of screening the inside of the biological body by the endoscopic scope, the high sensitivity observation image is generated in the signal processing unit, and at the time of precise inspecting for an interest area in the biological body, the high definition observation image is generated in the signal processing unit. N is a natural number equal to or more than 2.

According to the aspects of present invention, it is possible to observe a suitable image according to a use situation of an endoscopic apparatus because an observation image to be displayed in the monitor device is displayed as a high definition image at the time of precise inspecting and as a high sensitivity image at the time of screening.

BRIEF DESCRIPTION OF THE DRAWINGS

FIG. 11 is an explanatory diagram when the pixel addition is performed before the synchronization processing.

DETAILED DESCRIPTION OF EMBODIMENTS OF THE INVENTION

Hereinafter, an exemplary embodiment of the present invention will be described with reference to the accompanying drawings.

Figure 1:
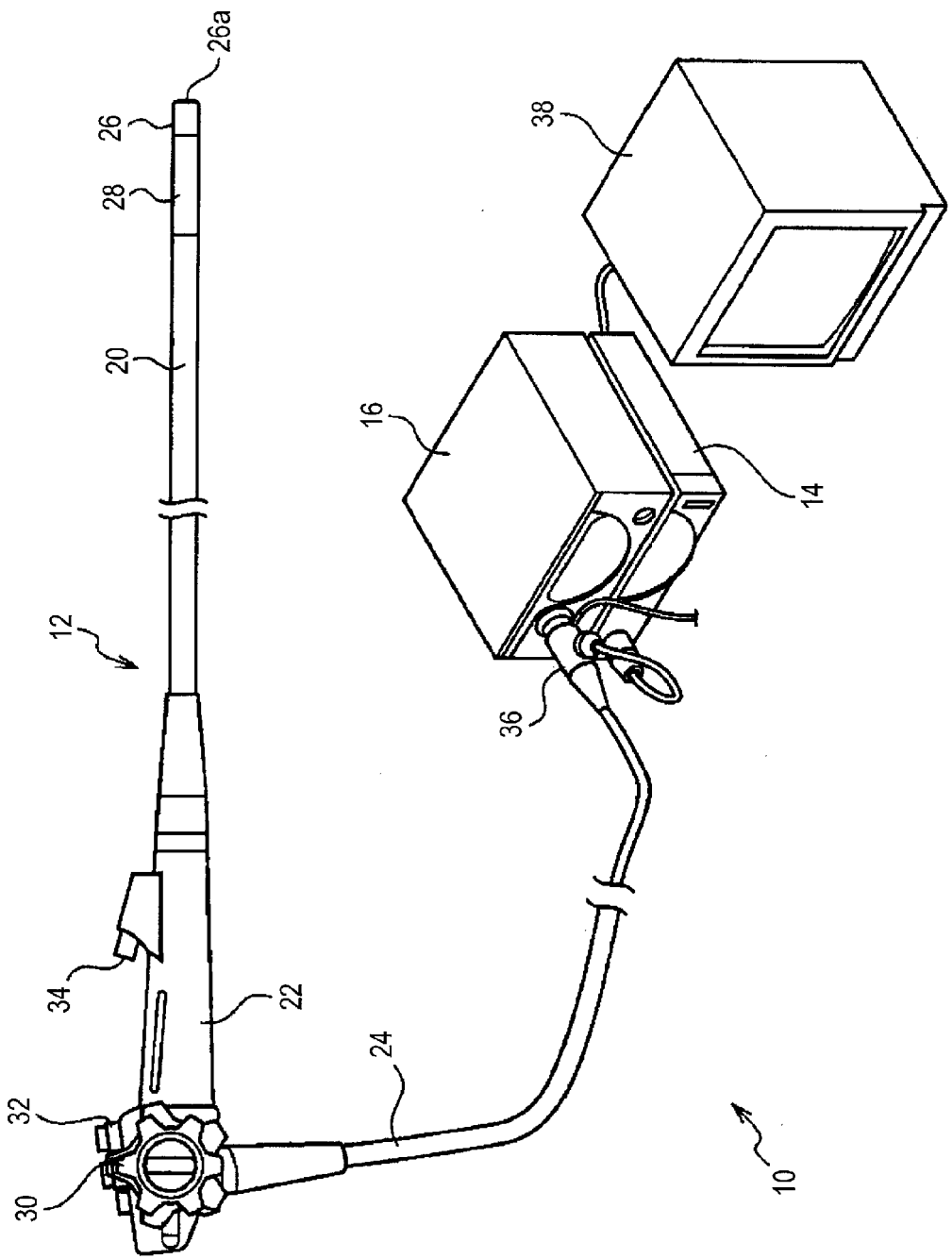
FIG. 1 is a system configuration view of an electronic endoscopic apparatus according to an exemplary embodiment of the present invention.

FIG. 1 is a system configuration view of an electronic endoscopic apparatus according to an exemplary embodiment of the present invention.

The electronic endoscopic apparatus (endoscope system) 10 of the present exemplary embodiment includes an endoscopic scope 12, and a processor device 14 and a light source device 16 that constitute a main body apparatus.

The endoscopic scope 12 includes a flexible inserting unit 20 that is inserted into a biological body (for example, a body cavity or stomach) of a patient (a subject), a manipulating unit 22 installed to be connected with a base end of the inserting unit 20, and a universal cord 24 that is connected with the processor device 14 and the light source device 16.

A front-end part 26 is continuously formed in the front-end of the inserting unit 20, an imaging chip 54 (see FIG. 3) for photographing the inside of the biological body is accommodated in the front-end part 26. A curved unit 28 formed by connecting a plurality of curved pieces is installed in the rear of the front-end part 26.

The curved unit 28 is curvedly operated in the up-down and left-right directions by pushing/pulling a wire provided by being inserted within the inserting unit 20 when an angle knob 30 installed in the manipulating unit 22 is manipulated. Therefore, the front-end part 26 faces a desired direction within the biological body.

A connector 36 is installed in the base end of the universal cord 24. The connector 36 is a complex type, and is connected to the light source device 16 as well as the processor device 14.

The processor device 14 supplies power to the endoscopic scope 12 via a cable 68 (see FIG. 3) inserted through the universal cord 24 to control the driving of the imaging chip 54, and at the same time, the processor device 14 receives an imaging signal transmitted from the imaging chip 54 via the cable 68, and performs various signal processings on the received imaging signal to convert into image data.

The image data converted in the processor device 14 is displayed in a monitor 38 as an endoscopic photographing image (an observation image). The monitor 38 is connected to the processor device 14 with a cable. The processor device 14 is also electrically connected to the light source device 16 via the connector 36, and generally controls the operations of the endoscope system 10 including the light source device 16.

Figure 2:
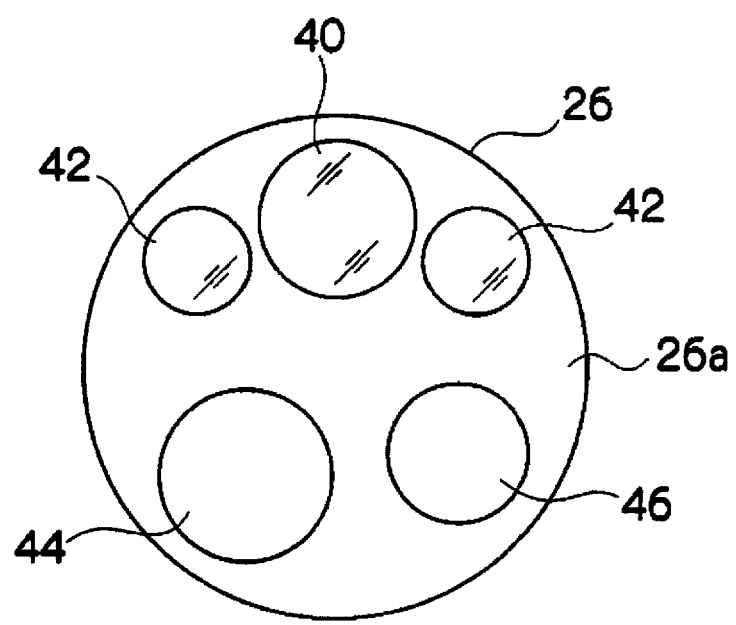
FIG. 2 is a front view of a front-end surface of the endoscopic scope illustrated in FIG. 1.

FIG. 2 is a front view illustrating a front-end surface 26a of the front-end part 26 of the endoscopic scope 12.

As illustrated in FIG. 2, an observation window 40, illuminating windows 42, a forceps outlet 44, an air/water transferring nozzle 46 are formed in the front-end surface 26a of the front-end part 26.

The observation window 40 is arranged at the center of the front-end surface 26a or a position offset from the center.

Two illuminating windows 42 are arranged in symmetric locations with respect to the observation window 40, and illuminate the light from the light source device 16 to the portion to be observed within the biological body.

The forceps outlet 44 is connected to a forceps channel (not illustrated) arranged within the inserting unit 20, and is communicated with a forceps inlet 34 (see FIG. 1) installed in the manipulating unit 22.

Various treatment tools, of which front-ends are provided with, for example, an injection needle or a high frequency mess, are inserted through the forceps inlet 34, and the front-ends of the various treatment tools come out from the forceps outlet 44 and into the biological body.

The air/water transferring nozzle 46 sprays cleaning water or air supplied from an air/water transferring device accommodated in the light source device 16 toward the inside of the biological body or the observation window 40 according to the manipulation of an air/water transferring button 32 (see FIG. 1) installed in the manipulating unit 22.

Figure 3:
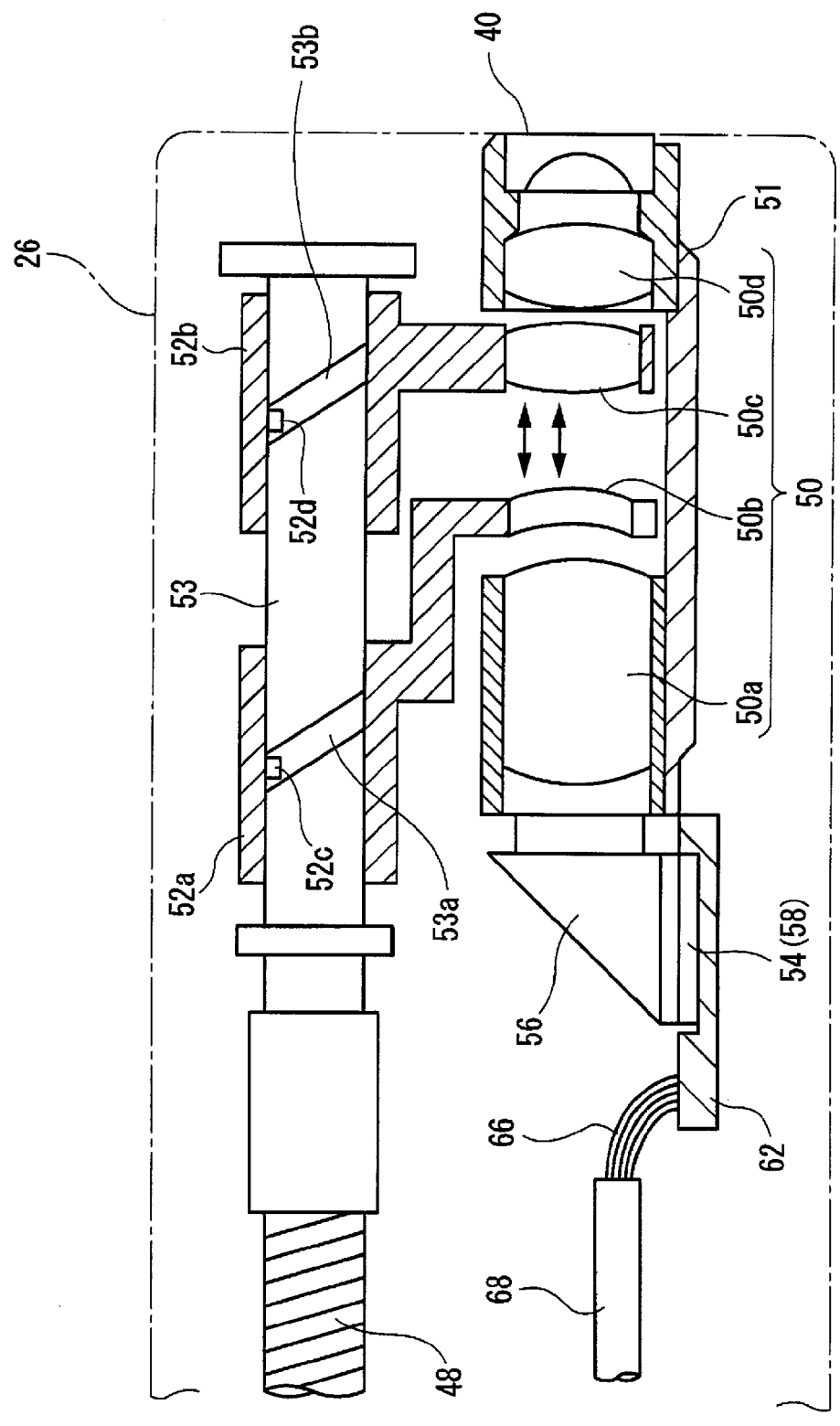
FIG. 3 is a longitudinal cross-sectional view of an imaging system of the front-end part of the endoscopic scope illustrated in FIG. 1.

FIG. 3 is a view illustrating the longitudinal cross-section of the imaging system of the front-end part 26 of the endoscopic scope 12.

As illustrated in FIG. 3, a barrel 51 is disposed inside the observation window 40. The barrel 51 maintains an object optical system 50 to receive an image light of a portion to be observed within the biological body.

The barrel 51 is attached such that the optic axis of the object optical system 50 is parallel to the center axis of the inserting unit 20. In the rear end of the barrel 51, a prism 56 is disposed which guides a light such that the image light of the portion to be observed is bent through the object optical system 50 at right angles to be directed to the imaging chip 54.

The imaging chip 54 is a monolithic semiconductor (a CMOS sensor chip) which is integrally formed with a CMOS type solid-state imaging device 58 (see FIG. 4) and a peripheral circuit that performs the driving and the input/output of the signals of the solid-state imaging device 58. The imaging chip 54 is mounted on a support substrate 62. The imaging surface (light receiving surface) of the solid-state imaging device 58 is arranged to face an exit surface of the prism 56.

The object optical system 50 of the present exemplary embodiment constitutes a zoom lens and includes movable lenses 50b, 50c in addition to fixed lenses 50a, 50d. The movable lenses 50b, 50c may move along the optical axis to change the distance between the movable lenses or the distance from the fixed lenses 50a, 50d. Therefore, the solid-state imaging device 58 may image an image of the portion to be observed which is enlarged in a desired magnification.

The movable lenses 50b, 50c are provided with cylindrical cam members 52a, 52b, respectively. Protrusions 52c, 52d are formed in the inner peripheral surfaces of the center holes of the cylindrical cam members 52a, 52b, respectively, and a cam shaft 53 is inserted through the center holes. In the circumference surface of the cam shaft 53, cam recesses 53a, 53b are engraved in which the protrusions 52c, 52d are slidably fitted, respectively.

As the cam shaft 53 is rotationally driven around the axis, the cylindrical cam members 52a, 52b move in the axis direction while rotating along the cam recesses 53a, 53b, and the movable lenses 50b, 50c move along the optic axis of the object optical system 50. The magnification of the object optical system 50, that is, a focus distance of the object optical system 50 is adjusted based on the rotational position of the cam shaft 53.

A power transferring wire 48 is attached to the base end of the cam shaft 53. The power transferring wire 48 is inserted up to the manipulating unit 22 in FIG. 1, and is rotated by a motor 49 (see FIG. 4) installed in the manipulating unit 22.

An operator of the endoscope may rotate the motor 49 forward/backward to enlarge/reduce the captured image by manipulating an enlarging/reducing instruction switch 22a (see FIG. 4) for the motor 49 installed in the manipulating unit 22.

The rear end of the support substrate 62 extending toward the rear end of the inserting unit 20 is provided with a plurality of input/output terminals to be parallel to the surface portion of the support substrate 62, and signal lines 66 are connected to the input/output terminals. The signal lines are used to relay the exchange of the various signals with the processor device 14 via the universal cord 24.

The plurality of signal lines 66 are integrally inserted in the flexible tube-shaped cable 68. The cable 68 is inserted into the inside of each of the inserting unit 20, the manipulating unit 22 and the universal cord 24, and is connected to the connector 36.

Although not illustrated in FIGS. 2 and 3, exit ends 120a of light guides 120 (see FIG. 4) that guide the illuminating light from the light source device 16 is disposed in the inner sides of the illuminating windows 42, respectively.

The light guides 120 constituted by binding a plurality of optical fibers, as in the cable 68, are inserted in the inside of each of the inserting unit 20, the manipulating unit 22 and the universal cord 24, respectively, and the incident ends of the light guides 120 are connected to the connector 36.

Figure 4:
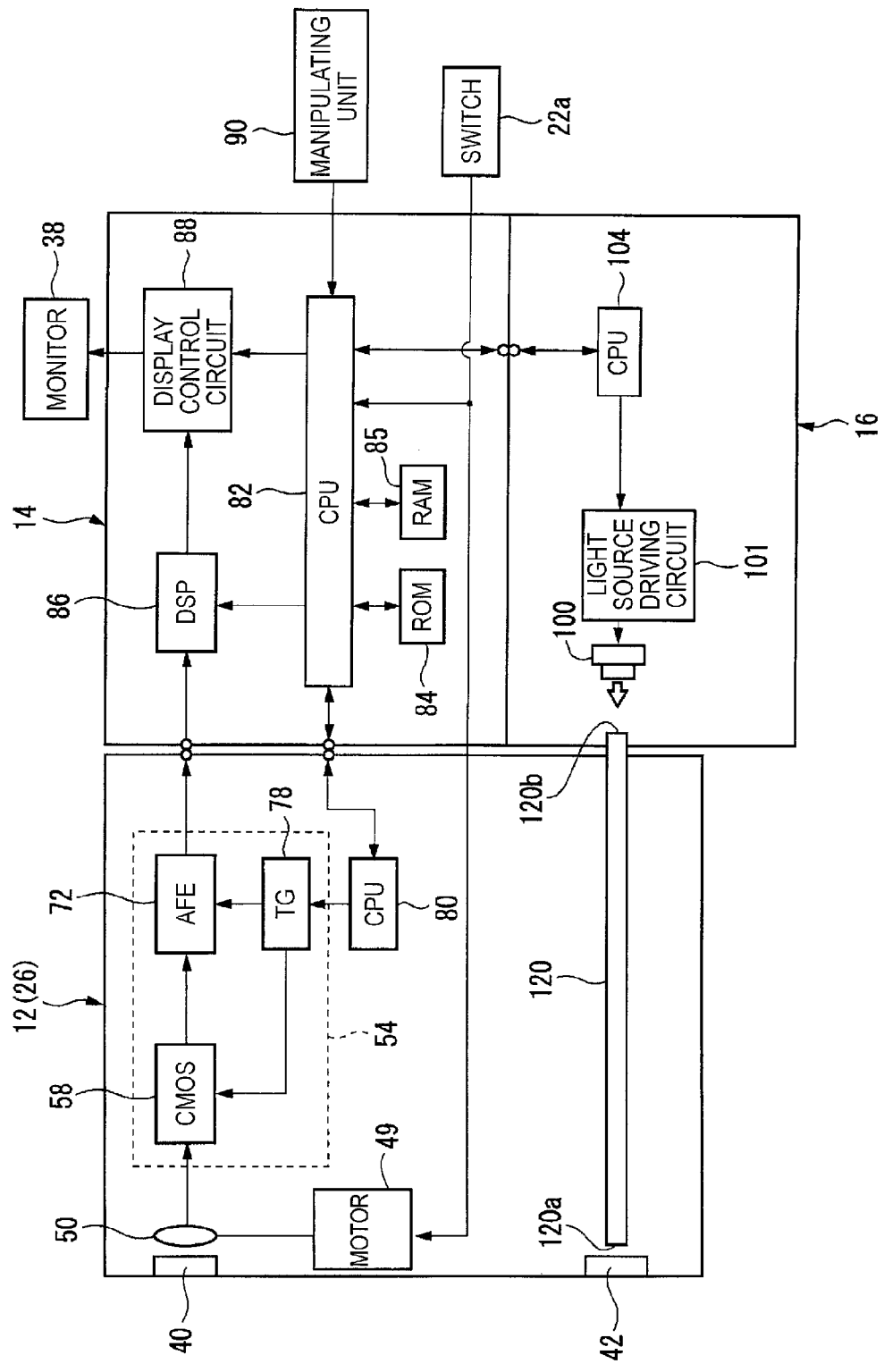
FIG. 4 is a functional block configuration diagram of the electronic endoscopic apparatus illustrated in FIG. 1.

FIG. 4 is a block diagram illustrating the electrical control system of the endoscope system 10.

As illustrated in FIG. 4, the imaging chip 54 is accommodated in the front-end part 26 of the endoscopic scope 12. The imaging chip 54 is constituted by the solid-state imaging device 58 and the peripheral circuit, and the peripheral circuit includes an analog signal processing circuit (analog front end; AFE) 72 and a timing generator (TG) 78. Further, a CPU 80 is provided which controls the peripheral circuit, and at the same time, exchanges information with a CPU 82 of the processor device 14.

The magnification of the object optical system 50 constituting the zoom lens is variably controlled by rotating the cam shaft 53 in FIG. 3 by the motor 49. The motor 49 is driven based on a signal of the enlarging/reducing instruction switch 22a, and at the same time, the information of the enlarging/reducing instruction is transferred to the CPUs 80, 82.

The TG 78 generates a driving pulse (for example, a vertical/horizontal scan pulse and a reset pulse) of the solid-state imaging device 58 and a synchronized pulse for the AFE 72, based on the control of the CPU 80. The solid-state imaging device 58 is driven according to the driving pulse inputted from the TG 78, and photoelectrically converts the optical shape imaged on the imaging surface through the object optical system 50 to output as an imaging signal.

A plurality of pixels are arranged in a matrix type in the imaging surface of the solid-state imaging device 58, and a photo sensor (photoelectric conversion device) is installed in each of the pixels. The light incident to the imaging surface of the solid-state imaging device 58 is accumulated in the photo sensor of each of the pixels as electrical charges. The signal electrical charges accumulated in the photo sensor of each of the pixels are sequentially read out as pixel signals and output in a predetermined frame rate by vertical and horizontal scanning using a vertical scan circuit and a horizontal scan circuit (both not illustrated).

Although not illustrated, each of the pixels of the solid-state imaging device 58 includes a color filter above a photoelectric conversion device. The color filter is constituted by a plurality of color segments, which are arranged in, for example, a Bayer arrangement. The solid-state imaging device 58 may be a CCD type device.

The AFE 72 is constituted by a correlated double sampling (CDS) circuit, an automatic gain circuit (AGC), and an A/D converter. The CDS circuit performs a correlated double sampling processing with respect to an imaging signal outputted from the solid-state imaging device 58 to remove an amp noise and a reset noise generated from the solid-state imaging device 58.

The AGC amplifies the imaging signal of which the noise is removed by the CDS circuit to a gain (amplifying rate) designated from the CPU 80. The A/D converter converts the imaging signal amplified by the AGC into a digital signal in a predetermined bit number, and outputs the converted signal. The imaging signal (digital imaging signal) digitalized and output from the AFE 72 is input to the processor device 14 via the signal lines 66.

The processor device 14 is configured to include the CPU 82, a ROM 84, a RAM 85, an image processing circuit (DSP) 86, and a display control circuit 88.

The CPU 82 controls each part of the processor device 14, and at the same time, generally controls the entire endoscope system 10. Various programs to control the operations of the processor device 14 or control data are stored in the ROM 84.

For example, programs executed by the CPU 82 or data are temporarily stored in the RAM 85.

The DSP 86 performs, for example, a color interpolation, a color separation, a color balance adjustment, a gamma adjustment, and an image enhancement processing to generate an image data with respect to the imaging signal imputed from the AFE 72 based on the control of the CPU 82, and at the same time, as described below, performs a pixel addition control according to the magnification of the captured image (the focus distance of the object optical system 50).

The image data output from the DSP 86 is input to the display control circuit 88, and the display control circuit 88 converts the image data input from the DSP 86 into a signal format corresponding to the monitor 38 to be displayed to the screen of the monitor 38.

The manipulating unit 90 of the processor device 14 is provided with a mode conversion button to select or convert the operation modes of the solid-state imaging device 58, or various buttons to receive other instruction inputs from user. A signal of the enlarging/reducing instruction switch 22a installed in the manipulating unit 22 of the endoscopic scope 12 is transferred to the motor 49 and transferred to the CPU 82 at the same time.

The light source device 16 is configured to include, for example, a white light emitting source 100, a light source driving circuit 101, and a CPU 104, and the incident ends 120b of the light guides 120 are installed to face the light emitting portion of the light emitting source 100.

The light emitting source 100 in the present exemplary embodiment may be optional, and may use a light source such as, for example, a LED light source, an organic light source, and a halogen lamp. A special light emitting source may be used as an auxiliary light source. The CPU 104 and the CPU 82 of the processor device 14 are connected to each other and exchange the information therebetween.

When the inside of the biological body is observed with the endoscope system 10 configured as described above, the power sources of the endoscopic scope 12, the processor device 14, the light source device 16, and the monitor 38 are turned ON, and the inserting unit 20 of the endoscopic scope 12 is inserted into the biological body. Then, the image of the inside of the biological body is observed with the monitor 38, which is imaged by the solid-state imaging device 58 while the inside of the biological body is being illuminated by the illuminating light passing through the light guides 120 from light source device 16.

The CPU 104 determines whether to control the light amount of the illuminating light from the captured image signal of the solid-state imaging device 58 based on the information exchanged between the CPU 104 and the CPU 82, and when the light amount control is performed, the CPU 104 sends an instruction to the light source driving circuit 101. The light source driving circuit 101 that receives the instruction from the CPU 104 controls the light emitting amount of the light source 100.

Figure 5A:
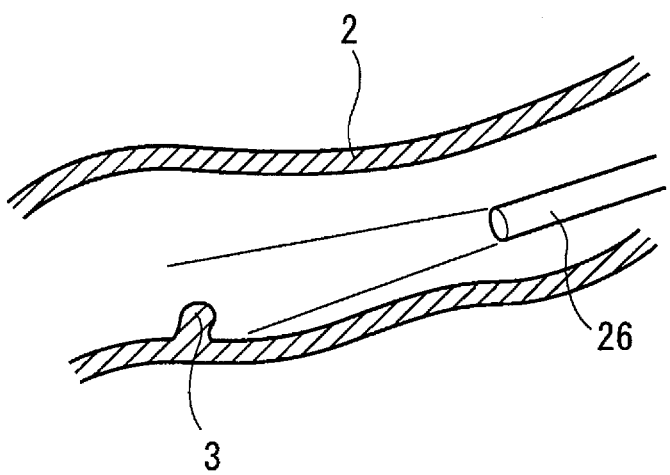
FIGS. 5A and 5B are views illustrating a relative positional relationship of the front-end part of the endoscopic scope and an interest area (an affected part) within a biological body.
Figure 5B:
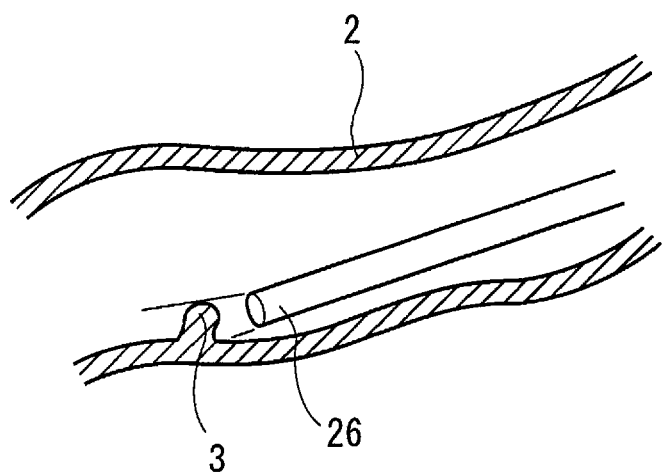

FIG. 5A illustrates a case where the front-end part 26 of the endoscopic scope 12 inserted within the biological body 2 is spaced far away from an affected part 3, and FIG. 5B illustrates a case where the front-end part 26 is positioned close to the affected part 3. When the light emitting amount of the illuminating light is made to be constant, the ratio of the brightness of the affected part 3 between the state where the affected part 3 is spaced far away from the front-end part 26 as illustrated in FIG. 5A and the where the affected part 3 is positioned close to the front-end part 26 as illustrated in FIG. 5B may be about 1:2000 to make it difficult to obtain a good image for the portion to be observed.

Therefore, the brightness of the illuminating light is controlled in consideration of a case where the observation image is imaged when the front-end part 26 of the endoscopic scope 12 is spaced far away from the affected part 3 or a case where the observation image is imaged when the front-end part 26 is positioned close to the affected part 3. The brightness of the illuminating light may be determined based on a captured image signal of the solid-state imaging device 58. When the observation image becomes darker than a predetermined brightness, the brightness is brightened by increasing the light emitting amount, and when the observation image becomes brighter than the predetermined brightness, the brightness is darkened by decreasing the light emitting amount of the illuminating light.

Figure 6:
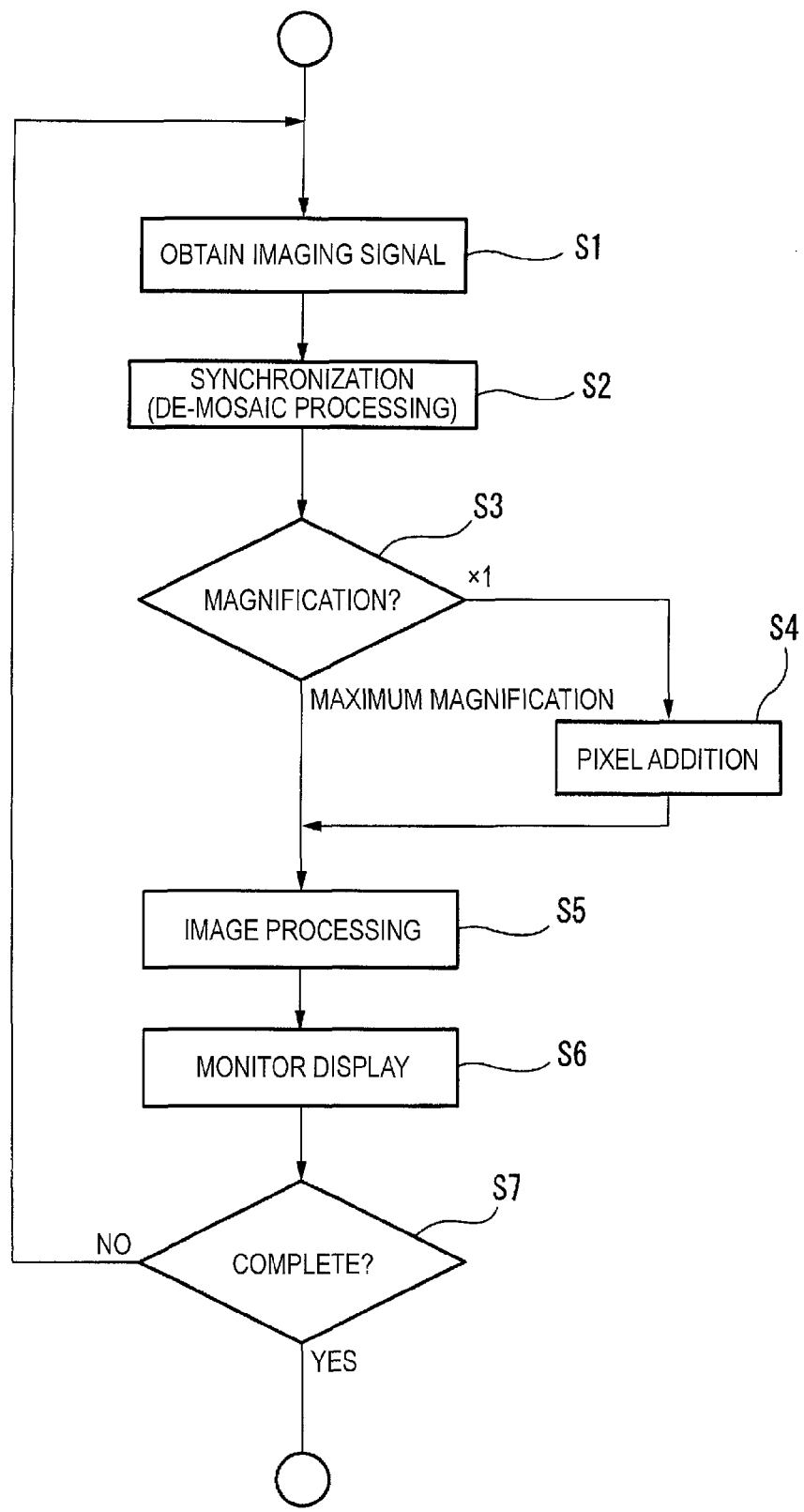
FIG. 6 is a flow chart illustrating a pixel addition control processing sequence according to an exemplary embodiment of the present invention.

In addition to the control of the light emitting amount, the present exemplary embodiment performs a pixel addition control as below. FIG. 6 is a flow chart illustrating a pixel addition control processing sequence performed by the CPU 82 in FIG. 4. The present exemplary embodiment will be described assuming that the magnification locations of the object optical system 50 as described in FIG. 3 are two locations of a standard location which is not enlarged and an enlarged location which is enlarged.

First, at step S1, the DSP 86 receives a captured image signal from the CMOS typed imaging device 58. At the next step S2, the DSP 86 performs a synchronization processing (de-mosaic processing). The synchronization processing indicates a processing that obtains three colors of R signal, G signal, and B signal at a position corresponding to each of the pixels. The synchronization processing will be described using FIG. 7.

Figures 7, 8:
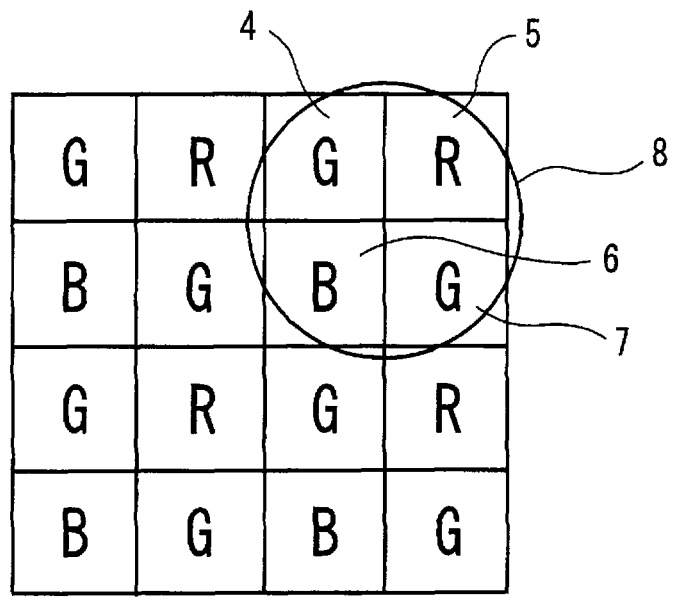
FIG. 7 is a view illustrating a synchronization processing and pixel addition of an imaging device.
FIG. 8 is a view illustrating an observational image obtained by the synchronization processing.

FIG. 7 is a view exemplifying a case where the pixel array of the imaging device 58 is a square lattice array and the color filter array is a Bayer array. In FIG. 7, "R" indicates a pixel on which a red filter is mounted (R pixel), "G" indicates a pixel on which a green filter is mounted (G pixel), and "B" indicates a pixel on which a blue filter is mounted (B pixel).

The R pixel detects a signal according to a light-receiving amount of the red color. The G pixel detects a signal according to a light-receiving amount of the green color. The B pixel detects a signal according to a light-receiving amount of the blue color.

That is, only a signal of a single color among the three colors of RGB is generated in a position corresponding to each of the pixels. As a result, the synchronization processing (de-mosaic processing) is performed to generate the signals of three colors of RGB in the position corresponding to each of the pixels.

For example, the G signal in a position corresponding to the G pixel 4 in FIG. 7 uses the G signal detected by the G pixel 4, the R signal in the same position is obtained by interpolating the detection signals of the R pixels near the G pixel 4, and the B signal in the same position is obtained by interpolating detection signals of the B pixels near the G pixel 4.

Similarly, the R signal in a position corresponding to the R pixel 5 uses the R signal detected by the R pixel 5, the G signal in the same position is obtained by interpolating the detection signals of the G pixels near the R pixel 5, and the B signal in the same position is obtained by interpolating the detection signals of the B pixels near the R signal 5. The processing is performed per each of the entire pixels.

With the synchronization processing, as illustrated in FIG. 8, one pixel data g1 to g16 constituted by a R signal, a G signal and a B signal, is generated in a position corresponding to each of the pixels of the solid-state imaging device, and an observation image with a high resolution is generated based on the pixel data corresponding to the entire pixels.

At the next step S3 in FIG. 6, the CPU 82 determines whether the magnification location of the object optical system 50 is in the standard location or in the enlarged location.

The medical practician who manipulates the endoscopic scope 12 performs a screening to inspect whether an abnormal portion exists or not while inserting the front-end part 26 of the endoscopic scope 12 into the biological body of the patient. The magnification location of the object optical system 50 at the time of screening is the standard location. During the screening, the medical practician finds out the affected part 3 in the state of FIG. 5A and positions the front-end part 26 of the endoscope close to the affected part 3, thereby developing the state of FIG. 5B.

During the screening, as illustrated in FIG. 5A, the light emitting amount of the illuminating light may be increased to illuminate a remote site brightly. However, the recent endoscopic scope 12 has a limitation in that in order to assure the small diameter of the endoscopic scope 12, the thickness of the light guide 120 cannot be increased excessively and in order to suppress the calorific power of the front-end part 26, the light emitting amount cannot be increased excessively. When the F-value of the object optical system 50 is increased to image a bright image, the depth of field is narrowed, which is unfavorable in screening.

Therefore, in the screening as described above, the procedure proceeds to step S4 of FIG. 6 where the DSP 86 in FIG. 4 performs a pixel addition, and then, proceeds to step S5.

The total pixel number of the conventional imaging devices used in the electronic endoscope was, for example, about 300,000 pixels, but the recent imaging devices that have been promoted to have an increased number of pixels have 800,000 to 3,000,000 pixels to meet the high resolution of the monitor 38. However, because the imaging device 58 is accommodated in the narrow front-end part 26 of the endoscope, it is difficult to increase the chip area of the imaging chip 54, and each pixel is more miniaturized. For this reason, the pixels in the bright illuminating light are saturated, and an image that looks white is imaged.

Although the endoscopic scope 12 of the present exemplary embodiment is equipped with an imaging chip 54 that is promoted to have an increased number of pixels, the high resolution observation image is not necessary at the time of screening. Since it is sufficient to realize the change in color of, for example, a rube, or the change in structure of, for example, a polyp, a two pixels addition or a four pixels addition may be performed to decrease the resolution, thereby improving the sensitivity. Therefore, it is possible to perform a good screening without increasing the light emitting amount, and without narrowing the depth of field.

The pixel addition performed at step S4 will be described.

A pixel addition means a processing that divides the entire pixels included in the solid-state imaging device into groups of n pixels (n is a natural number equal to or more than 2), and generates R signal, G signal and B signal for each of the groups.

For example, sixteen pixels illustrated in FIG. 7 are divided into groups of four adjacent pixels. In the example of FIG. 7, four pixels surrounded by a circle 8 form a group. In a position corresponding to each of the four pixels surrounded by the circle 8, R signal, G signal, and B signal are generated by the synchronization processing.

The DSP 86 performs an addition for the R signals generated in a position corresponding to each of the four pixels surrounded by the circle 8, and sets an R signal after the addition as the R signal of the position corresponding to each of the four pixels.

The DSP 86 performs an addition for the G signals generated in a position corresponding to each of the four pixels surrounded by the circle 8, and sets a G signal after the addition as the G signal of the position corresponding to each of the four pixels.

The DSP 86 performs an addition for the B signals generated a the position corresponding to each of the four pixels surrounded by the circle 8, and set a B signal after the addition as the B signal of the position corresponding to each of the four pixels.

The DSP 86 performs the processing as described above for all the groups.

Figures 9, 10:
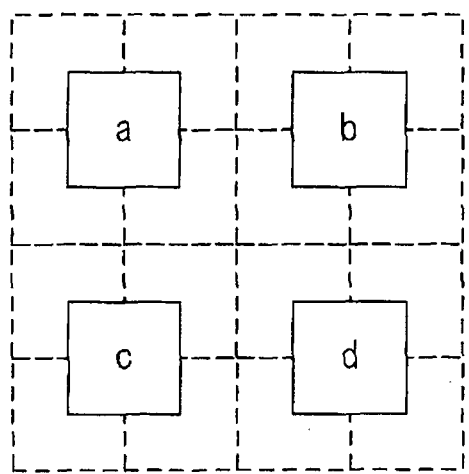
FIG. 9 is a view illustrating an observational image obtained by the pixel addition.
FIG. 10 is a view illustrating an observational image obtained by the pixel addition.

Accordingly, as illustrated in FIG. 9, per every four pixels, the pixel data (a~d) of the positions respectively corresponding to the four pixels become the same. That is, the same pixel data is generated for each of the groups, and the brightness of the pixel data becomes about four times of the brightness of the pixel data constituting the high resolution observation image. In this way, by performing the pixel addition, it is possible to obtain a high sensitivity observation image, of which the resolution is one-fourth times of that of a high definition observation image obtained by the synchronization processing and of which the sensitivity is four times of that of the high definition observation image.

In the above description, the number of the total pixel data of the high sensitivity observation image is made to be the same as that of the high resolution observation image by making the same four pixel data correspond to each group. Accordingly, even if the pixel addition was performed, the high sensitive observation image may be displayed to fill the screen of the monitor without decreasing the size of the observation image.

Of course, as illustrated in FIG. 10, the number of the total pixel data of the high sensitivity observation image may be one-fourth of that of the high resolution observation image by generating the pixel data (a~d) in a position corresponding to the center of gravity of the four pixels constituting each group.

It may be said that the high sensitivity observation image generated by the above pixel addition is configured by image data corresponding to that formed by dividing the pixel data constituting the high definition observation image into groups of n data and combining them.

For example, in FIGS. 9 and 10, the pixel data a constituting the high sensitivity observation image corresponds to that formed by combining the pixel data g1~g4 in FIG. 8, the pixel data b constituting the high sensitivity observation image corresponds to that formed by combining the pixel data g5~g8 in FIG. 8, the pixel data c constituting the high sensitivity observation image corresponds to that formed by combining the pixel data g9~g12 in FIG. 8, and the pixel data d constituting the high sensitivity observation image corresponds to that formed by combining the pixel data g13~g16 in FIG. 8.

As illustrated in FIG. 5B, when the front-end part 26 of the scope is positioned close to the interest area such as, for example, the affected part 3 by screening, the light emitting amount of the illuminating light is controlled to be decreased in such manner that the observation image of the affected part 3 does not become white by saturation.

Then, a doctor precisely inspects the affected part 3. The precise inspection is performed by setting the magnification location of the object optical system 50 to an enlarged location such that an enlarged image is displayed on the monitor 38. That is, when, as a result of the determination in step S3 of FIG. 6, the magnification location is the enlarged location, the procedure proceeds from step S3 to step S5.

At step S5, the DSP 86 performs an image processing such as, for example, a gamma correction processing or an RGB/YC conversion processing in addition to the de-mosaic processing, and in the next step S6, the CPU 82 displays the captured image (observation image) after the image processing on the monitor 38.

That is, when the procedure proceeds from step S3 to step S5, the high definition image is displayed on the monitor 38 without performing the pixel addition to obtain the high definition image. Accordingly, for example, a fine blood vessel structure is enabled to be depicted.

In the next step S7, the CPU 82 determines whether the use of the endoscopic scope is completed. When completed, the CPU 82 completes the present processing, and when not completed, the CPU 82 returns to step S1 to repeat the processings as described above.

In the above described exemplary embodiment, descriptions have been made as to the case where the magnification locations of the object optical system 50 are two locations of the standard location and the enlarged location. However, when the magnification locations are, for example, a standard location (not enlarged), a two times-enlarged location, and a four times-enlarged location, and hence the enlarged magnification is variable, it is possible to perform a four pixels addition (n=4) in the standard location, perform a two pixels addition (n=2) in the two times-enlarged location, and perform no pixel addition in the four times-enlarged location.

In the above described exemplary embodiment, a high sensitivity observation image is generated by performing a signal addition after a synchronization processing, but not limited thereto.

For example, signal charges of the same color component may be added in a signal charge state in the inside of the solid-state imaging device or the same color signals may be added before performing the synchronization processing.

Figure 11:
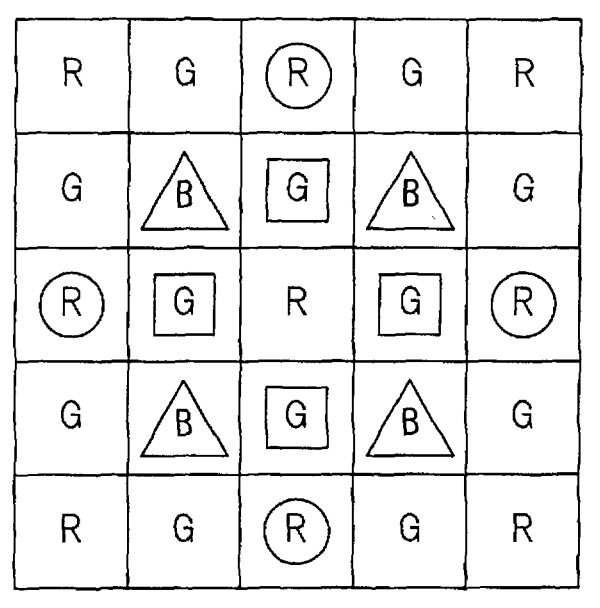

For example, when twenty-five (5 by 5) pixels as illustrated in FIG. 11 is set to one group and pixel data of one type are generated to correspond to the group, the CPU 82 controls the imaging chip 54 such that the detection signals of four R pixels surrounded by "○" in FIG. 11 are added in the inside of the solid-state imaging device or in the AFE 72, the detection signals of four B pixels surrounded by "□" in FIG. 11 are added in the inside of the solid-state imaging device or in the AFE 72, and the detection signals of four G pixels surrounded by "□" in FIG. 11 are added in the inside of the solid-state imaging device or in the AFE 72.

The pixel data of the observation image obtained by performing the synchronization processing for the captured image signal outputted to the DSP 86 by the control as described above may correspond to that formed by dividing the pixel data constituting the high definition observation image, which is obtained by capturing the signals from the entire pixels of the solid-state imaging device and performing the synchronization processing, into groups of four pixels and combining them. Therefore, a high definition observation image may also be generated in the DSP 86 when the CPU 82 performs the above-described control.

As described above, in relation to the DSP 86, the CPU 82 performs control for generating a high definition observation image and a high sensitivity observation image that is constituted by pixel data corresponding to that obtained by dividing pixel data that constitutes the high definition observation image into groups of n pixels and combining them.

Meanwhile, when the signal addition is performed before the synchronization processing, the adding number of the R signal, the adding number of the G signal, and the adding number of the B signals may be changed for every color rather than being the same.

An endoscope may illuminate not only the white light but also a light of special wavelength as an illuminating light. In such a case, it is possible to obtain an image that emphasizes, for example, a lesion of an interest area may be obtained by changing the adding number for each of the colors of filters mounted on pixels.

Although FIG. 4 illustrates a configuration where the CPU 82 receives the information of a switch position of the manipulating switch 22a, a configuration may be acceptable where a rotation position of the cam shaft 53 is directly detected by a sensor and the detected information is transferred to the CPU 82 through the CPU 80.

In the above description, the CPU 82 determines that it is a time for precise inspecting when the enlarged magnification determined by the position of a zoom lens is the maximum, and determines that it is a time for screening when the enlarged magnification is not the maximum magnification, but is not limited thereto.

For example, the CPU 82 may determine that it is a time for screening when the enlarged magnification is equal to or less than a predetermined value (a value between the maximum magnification and the minimum magnification (a middle magnification)), and may determine that is a time for precise inspecting when the enlarged magnification is more than the predetermined value.

In a real clinic technique, the depth of field becomes narrowed in the maximum enlarged magnification. Therefore, a screening may be performed in an area where the magnification is equal to or lower than the middle magnification and hence the depth of field is relatively wide, and a magnification higher than the middle magnification may be used at the precise inspecting. Accordingly, as the CPU 82 makes determinations as described above, the control according to the real clinic technique is enabled.

Meanwhile, the value of the middle magnification may be optionally set based on, for example, the preference according to the user. The middle magnification may be equal to the minimum enlarged magnification.

Further, in the above description, the CPU 82 determines whether it is a time for screening or for precise inspecting based on the location of the zoom lens, but is not limited thereto. For example, the information indicating the time for screening or the time for precise inspecting may be inputted by the manipulating unit 90, and the CPU 82 may determine whether it is a time for screening or for precise inspecting based on the inputted information.

In addition, an acceleration sensor may be installed in the front-end part 26 of the endoscopic scope 12, and the CPU 82 may measure the moving speed of the front-end part 26 from the information of the acceleration sensor. Then, when the speed is equal to or more than a threshold value, the CPU 82 may determine that it is a time for screening, and when the speed is less than the threshold value, the CPU 82 may determine that it is a time for precise inspecting.

Further, when a high sensitivity observation image is generated in the DSP 86, the CPU 82 may change the value of n in the areas where the reflection light of the illuminating light that illuminates the subject within the biological body is dark and bright, rather than setting the value of n to be the same in the entire observation image.

For example, the CPU 82 determines the brightness for an observation image obtained by the synchronization processing. For a dark area, the CPU 82 generates a high sensitivity observation image configured by the pixel data corresponding to those obtained by dividing the pixel data constituting a high definition observation image into groups of, for example, four and combining them, and for a bright area, the CPU 82 generates a high sensitivity observation image configured by the pixel data corresponding to those obtained by dividing the pixel data constituting the high definition observation image into groups of, for example, two and combining them.

With regard to the observation image configured by pixel data of 4 by 4 as illustrated in FIG. 8, it is assumed that the area of pixel data g5~g8 is the bright area, and the others are the dark areas.

In that event, with respect to the DSP 86, the CPU 82 generates a high sensitivity observation image which is configured by pixel data a formed by combining the pixel data g1~g4, pixel data b formed by combining the pixel data g5 and g6, pixel data c formed by combining the pixel data g9~g12, and pixel data d formed by combining the pixel data g13~g16.

The method of changing the sensitivity (brightness) of an observation image according to the brightness of a subject in this manner may adopt one of the known methods disclosed in, for example, JP-2008-072501 A, JP-2007-251694 A and JP-H11-313247 A.

As described above, the following matters are disclosed herein.

The disclosed electronic endoscopic apparatus includes: an endoscopic scope inserted into a biological body; an imaging device accommodated in the front-end part of the endoscopic scope; a signal processing unit that processes a captured image signal by the imaging device to generate an observation image; a monitor device that displays the observation image; and a control unit that controls the signal processing unit to generate a high definition observation image and a high sensitivity observation image as the observation image, the high sensitivity observation image being constituted by pixel data corresponding to those obtained by dividing the pixel data constituting the high definition observation image into n (n is a natural number equal to or more than 2) and combining them. The control unit makes the signal processing unit generate the high sensitivity observation image at the time of screening the inside of the biological body by the endoscopic scope, and generate the high definition observation image at the time of precise inspecting for an interest area in the biological body.

The disclosed electronic endoscopic apparatus further includes a zoom lens installed in the front end of the imaging device. The control unit determines whether it is a time for precise inspecting or for screening based on the magnification decided by the location of the zoom lens.

In the disclosed electronic endoscopic apparatus, when the enlarged magnification decided by the zoom lens is equal to or less than a predetermined value smaller than the maximum enlarged magnification, the control unit determines that it is a time for screening, and when the enlarged magnification is more than the predetermined value, the control unit determines that it is a time for precise inspecting.

In the disclosed electronic endoscopic apparatus, when the zoom lens is disposed in the maximum enlarged location, the control unit determines that it is a time for precise inspecting, and when the zoom lens is disposed in a location other than the maximum enlarged location, the control unit determines that is a time for screening.

In the disclosed electronic endoscopic apparatus, the control unit generates an image where the higher the enlarged magnification, the smaller the value of the n, as the high sensitivity observation image.

In the disclosed electronic endoscopic apparatus, the control unit generates a high sensitivity observation image, the number n of which is set to be larger in an area where the reflection light of the light illuminating the subject within the biological body is dark, than in an area where the reflection light is bright.

The disclosed method of controlling an electronic endoscopic apparatus in such a manner that an observation image is generated by a signal processing unit that processes a captured image signal from an imaging device accommodated in the front-end part of an endoscopic scope to be inserted into a biological body, and is displayed on a monitor device. The method includes: controlling the signal processing unit to generate a high definition observation image and a high sensitivity observation image as the observation image. The high sensitivity observation image is constituted by pixel data corresponding to those obtained by dividing the pixel data constituting the high definition observation image into n (n is a natural number equal to or more than 2) and combining them. At the controlling step, at the time of screening the inside of the biological body by the endoscopic scope, the high sensitivity observation image is generated in the signal processing unit, and at the time of precise inspecting for an interest area in the biological body, the high definition observation image is generated in the signal processing unit.

What is claimed is:

1. An electronic endoscopic apparatus comprising:
   an endoscopic scope that is insertable into a biological body;
   an imaging device that is provided in the front-end part of the endoscopic scope;
   a signal processing unit that processes a captured image signal obtained by the imaging device to generate an observation image;
   a monitor device that displays the observation image; and
   a control unit that controls the signal processing unit to generate a high definition observation image and a high sensitivity observation image as the observation image, the high sensitivity observation image being constituted by pixel data corresponding to those obtained by combining n data selected from pixel data constituting the high definition observation image as one set,
   wherein the control unit makes the signal processing unit generate the high sensitivity observation image at the time of screening the inside of the biological body by the endoscopic scope, and generate the high definition observation image at the time of precise inspecting for an interest area in the biological body, and
   n is a natural number equal to or more than 2.

2. The electronic endoscopic apparatus according to claim 1 further comprising a zoom lens that is installed in the front end of the imaging device,
   wherein the control unit determines whether it is a time for precise inspecting or for screening based on the magnification decided by the location of the zoom lens.

3. The electronic endoscopic apparatus according to claim 2, wherein, when the enlarged magnification decided by the zoom lens is equal to or less than a predetermined value smaller than the maximum enlarged magnification, the control unit determines that it is a time for screening, and when the enlarged magnification is more than the predetermined value, the control unit determines that it is a time for precise inspecting.

4. The electronic endoscopic apparatus according to claim 2, wherein, when the zoom lens is disposed in the maximum enlarged location, the control unit determines that it is a time for precise inspecting, and when the zoom lens is disposed in a location other than the maximum enlarged location, the control unit determines that it is a time for screening.

5. The electronic endoscopic apparatus according to claim 3, wherein the control unit generates an image where the higher the enlarged magnification, the smaller the value of the n, as the high sensitivity observation image.

6. The electronic endoscopic apparatus according to claim 1, wherein the control unit generates a high sensitivity observation image, the number n of which is set to be larger in an area where the reflection light of the light illuminating the subject within the biological body is dark, than in an area where the reflection light is bright.

7. A control method of an electronic endoscopic apparatus in which an observation image is generated by a signal processing unit that processes a captured image signal from an imaging device accommodated in the front-end part of an endoscopic scope insertable into a biological body, and is displayed on a monitor device, the method comprising:

controlling the signal processing unit to generate a high definition observation image and a high sensitivity observation image as the observation image, the high sensitivity observation image being constituted by pixel data corresponding to those obtained by combining n data among pixel data constituting the high definition observation image as one set, wherein, at the controlling step, at the time of screening the inside of the biological body by the endoscopic scope, the high sensitivity observation image is generated in the signal processing unit, and at the time of precise inspecting for an interest area in the biological body, the high definition observation image is generated in the signal processing unit, and n is a natural number equal to or more than 2.

* * * * *